United States Patent
Scheib et al.

(10) Patent No.: US 9,750,522 B2
(45) Date of Patent: Sep. 5, 2017

(54) SURGICAL INSTRUMENT WITH CLIPS HAVING TRANSECTING BLADES

(71) Applicant: Ethicon Endo-Surgery, Inc., Cincinnati, OH (US)

(72) Inventors: Charles J. Scheib, Loveland, OH (US); Mark D. Overmyer, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 806 days.

(21) Appl. No.: 13/967,578

(22) Filed: Aug. 15, 2013

(65) Prior Publication Data

US 2015/0048142 A1   Feb. 19, 2015

(51) Int. Cl.
| | | |
|---|---|---|
| A61B 17/068 | (2006.01) | |
| A61B 17/128 | (2006.01) | |
| A61B 17/32 | (2006.01) | |
| A61B 17/064 | (2006.01) | |
| A61B 17/122 | (2006.01) | |
| A61B 18/14 | (2006.01) | |
| A61B 18/00 | (2006.01) | |

(52) U.S. Cl.
CPC .... *A61B 17/320092* (2013.01); *A61B 17/064* (2013.01); *A61B 17/068* (2013.01); *A61B 17/122* (2013.01); *A61B 17/1285* (2013.01); *A61B 17/320068* (2013.01); *A61B 18/1445* (2013.01); *A61B 2017/0641* (2013.01); *A61B 2017/0645* (2013.01); *A61B 2017/1225* (2013.01); *A61B 2018/0063* (2013.01); *A61B 2018/00601* (2013.01); *A61B 2018/1415* (2013.01)

(58) Field of Classification Search
CPC ... A61B 17/122; A61B 17/064; A61B 17/128; A61B 17/32; A61B 17/068
USPC ........................ 227/175.1–180.1; 606/49, 51
See application file for complete search history.

(56) References Cited

U.S. PATENT DOCUMENTS

| | | |
|---|---|---|
| 4,805,823 A | 2/1989 | Rothfuss |
| 5,415,334 A | 5/1995 | Williamson, IV et al. |
| | (Continued) | |

FOREIGN PATENT DOCUMENTS

| | | |
|---|---|---|
| EP | 0 121 475 A2 | 10/1984 |
| EP | 0 565 822 A2 | 10/1993 |
| | (Continued) | |

OTHER PUBLICATIONS

Partial European Search Report dated Dec. 5, 2014 for Application No. EP 14181055.6, 6 pgs.

(Continued)

*Primary Examiner* — Hemant M Desai
*Assistant Examiner* — Mary Hibbert
(74) *Attorney, Agent, or Firm* — Frost Brown Todd LLC

(57) ABSTRACT

A transecting fastener is operable to cut and secure tissue. The transecting fastener comprises a plurality of legs configured to grip tissue. The transecting fastener further comprises a crown portion and at least one blade. The crown portion joins the plurality of legs and is malleable. The at least one blade is positioned on each of the plurality of legs. The at least one blade is operable to cut tissue. A fastener deploying instrument may be used to deploy the transecting fastener. The fastener deploying instrument may deploy the fasteners in parallel pairs, in an end to end manner.

16 Claims, 14 Drawing Sheets

(56) References Cited

U.S. PATENT DOCUMENTS

| | | |
|---|---|---|
| 5,465,895 A | 11/1995 | Knodel et al. |
| 5,597,107 A | 1/1997 | Knodel et al. |
| 5,632,432 A * | 5/1997 | Schulze ............ A61B 17/07207 227/176.1 |
| 5,673,840 A | 10/1997 | Schulze et al. |
| 5,704,534 A | 1/1998 | Huitema et al. |
| 5,814,055 A | 9/1998 | Knodel et al. |
| 5,906,625 A | 5/1999 | Bito et al. |
| 6,645,205 B2 | 11/2003 | Ginn |
| 6,945,444 B2 | 9/2005 | Gresham et al. |
| 6,978,921 B2 | 12/2005 | Shelton, IV et al. |
| 7,000,818 B2 | 2/2006 | Shelton, IV et al. |
| 7,143,923 B2 | 12/2006 | Shelton, IV et al. |
| 7,303,108 B2 | 12/2007 | Shelton, IV et al. |
| 7,367,485 B2 | 5/2008 | Shelton, IV et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,434,715 B2 | 10/2008 | Shelton, IV et al. |
| 7,721,930 B2 | 5/2010 | McKenna et al. |

FOREIGN PATENT DOCUMENTS

| | | | |
|---|---|---|---|
| EP | 1 943 965 A2 | 7/2008 | |
| WO | WO 94/24949 | 10/1984 | |
| WO | WO 2012129317 A2 * | 9/2012 | ............ A61B 17/122 |

OTHER PUBLICATIONS

European Search Report and Written Opinion dated Mar. 24, 2015 for Application No. EP 14181055.6, 9 pgs.
International Search Report dated Mar. 19, 2015 for Application No. PCT/US2014/050665, 8 pgs.
International Preliminary Report on Patentability and Written Opinion dated Feb. 16, 2016 for Application No. PCT/US2014/050665, 10 pgs.

* cited by examiner

SURGICAL INSTRUMENT WITH CLIPS HAVING TRANSECTING BLADES

BACKGROUND

During some surgical procedures, it may be necessary to cut a portion of tissue. When tissue is cut, bleeding may occur, which the physician may wish to stop at about the same time the tissue is cut. Endocutters with surgical staples provide a way of cutting tissue and stapling tissue in a substantially simultaneous manner, with the staples being applied adjacent to the tissue transection to hold together transected layers of tissue and provide hemostasis. Endocutters may include reloadable staple cartridges, which in some instances may be undesirable as the operator may need to repeatedly reload staple cartridges to transect and staple along a long transection path. Furthermore, the use of reloadable cartridges may also require that the user remove the endocutter from the patient between actuations to reload the device.

Examples of surgical staplers are described in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; and U.S. Pat. No. 7,721,930, entitled "Disposable Cartridge with Adhesive for Use with a Stapling Device," issued May 25, 2010. The disclosure of each of the above-cited U.S. patents is incorporated by reference herein. While the surgical staplers referred to above are described as being used in endoscopic procedures, it should be understood that such surgical staplers may also be used in open procedures and/or other non-endoscopic procedures.

While several surgical instruments have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
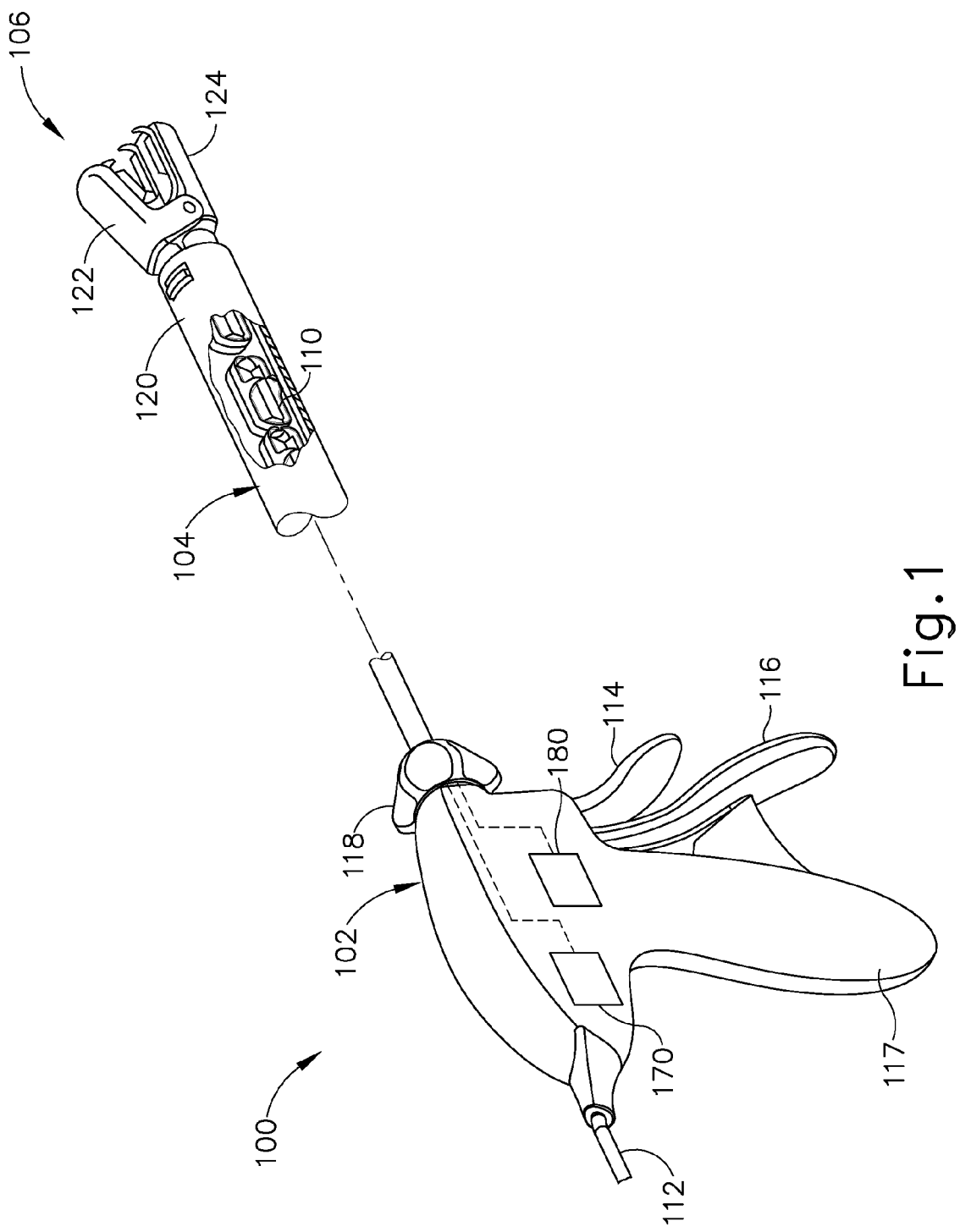
FIG. 1 depicts a top, perspective view of an exemplary applier for applying transecting fasteners.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a robotic surgical driver comprising a proximal housing having an interface that mechanically and electrically couples with a surgical instrument having a distal surgical end effector. The term "proximal" refers the position of an element closer to the robotic surgical driver housing and the term "distal" refers to the position of an element closer to the surgical end effector of the surgical instrument and further away from the housing.

I. Exemplary Surgical Instrument

FIG. 1 depicts an exemplary surgical instrument (100) that is operable to cut and seal tissue. In particular, in many instances, such tissue may include tissue having multiple layers that the user wishes to cut and seal. For instance two or more layers of tissue may need to be cut and fastened together. In other instances, just a single layer of tissue may be cut and sealed at the cut. Surgical instrument (100) may be hand held by a user and then actuated to simultaneously cut and seal tissue. In some instances, surgical instrument (100) may be inserted through a trocar to access a portion of the patient's body, but in other instances, surgical instrument (100) may be inserted directly into a surgical region for cutting and stapling tissue in an open procedure. Generally, a user may access a surgical site and position surgical instrument (100) to cut and seal tissue. To cut and seal tissue, one or more transecting fasteners (110) may be advanced through surgical instrument (100) toward the surgical site and thereafter clamped onto tissue. Surgical instrument (100) may then actuate to close fasteners (110), to thereby simultaneously transect and fasten tissue. This process will be described in further detail below.

Surgical instrument (100) comprises a handpiece (102), shaft (104), and end effector (106). Handpiece (102) has a pistol grip shape operable to be hand held by the user, but it will be appreciated that handpiece (102) may have any suitable shape as would be apparent to one of ordinary skill in the art in view of the teachings herein. For instance, rather than a pistol grip, handpiece (102) may have a scissor grip, may be shaped as a hand held shaft, or may even be configured for integration into a mounted machine or robotic arm for controlling surgical instrument (100). Handpiece (102) comprises a cord or cable (112), closure trigger (116), a grip (117), an energy trigger (114), and rotation knob (118). In some instances, examples of which will be described below, handpiece (102) may also comprise an RF generator (170) or ultrasonic transducer (180). Cord (112) and energy trigger (114) may be optional depending on whether RF generator (170) and ultrasonic transducer (180) are used.

Cord (112) is operable to provide energy to surgical instrument (100) in the event that surgical instrument (100) uses energy either to provide RF energy to the surgical site through RF generator (170) or to power ultrasonic transducer (180) to provide ultrasonic vibrations to the surgical site. It will be understood that surgical instrument (100) need not necessarily be electrically driven. Furthermore, in some instances, rather than having cord (112) to deliver power for surgical instrument (100), surgical instrument (100) may incorporate a battery pack or other similar portable power source operable to deliver power. In some versions, surgical instrument (100) is powered solely by user actuation (e.g., by the user manipulating closure trigger (116)), such that surgical instrument (100) may lack cord (112), a battery, or other source of electrical power.

Energy trigger (114) is operable to be actuated by the user to selectively activate a feature at end effector (106). For instance, squeezing energy trigger (114) may be used to power a portion of surgical instrument (100) through cord (112). While the exemplary version shows energy trigger (114) having a trigger structure, it will be understood that any suitable structure for energy trigger (114) may be used as would be apparent to one of ordinary skill in the art in view of the teachings herein. In some instances, as was mentioned above, energy trigger (114) and cord (112) need not be included at all if surgical instrument (100) is entirely mechanically operated.

Closure trigger (116) is in communication with end effector (106) such that the user squeezing closure trigger (116) causes end effector (106) to close. In the exemplary version, closure trigger (116) is operable to be actuated by squeezing closure trigger (116) toward grip (117). However, it will be understood that closure trigger (116) may take any suitable form including a button, knob, etc. Other suitable structures for closure trigger (116) will be apparent to those of ordinary skill in the art in view of the teachings herein.

Rotation knob (118) is in communication with handpiece (102) and is further in communication with shaft (104). Rotation knob (118) may be manually rotated by a user and is shaped to facilitate gripping by the user. Rotation knob (118) is rotationally coupled with shaft (104) as well as end effector (106) such that rotating rotation knob (118) is operable to rotate end effector (106). Furthermore, shaft (104) rotates with end effector (106) such that rotating rotation knob (118) causes both shaft (104) and end effector (106) to rotate. More specifically, knob (118), shaft (104), and end effector (106) all rotate about the longitudinal axis defined by shaft (104). For instance, in the event that the user may wish to position end effector (106) differently in relation to tissue to be cut and sealed, the user may rotate rotation knob (118) to rotate end effector (106).

Shaft (104) extends distally from handpiece (102). In the exemplary version, shaft (104) is shown with a straight profile extending outward from handpiece (102) without a curve, but it will be appreciated that in some versions, shaft (104) may have a curved profile or any other suitable shape as would be apparent to one of ordinary skill in the art in view of the teachings herein. Shaft (104) is further operable to house a plurality of transecting fasteners (110), which will be described in further detail below. Shaft (104) also comprises an outer tube (120). Outer tube (120) is operable to longitudinally translate relative to the rest of shaft (104) as a result of the user actuating closure trigger (116). By way of example only, closure trigger (116) may be in communication with shaft (104) through a plurality of internal linkages, a rack and pinion system, or any other suitable ways of mechanically coupling closure trigger (116) and shaft (104) as would be apparent to one of ordinary skill in the art in view of the teachings herein. Outer tube (120) is in further communication with end effector (106). Outer tube (120) is operable generally to control the opening and closing of end effector (106), which will be described in further detail below.

II. Exemplary End Effector

Figure 3:
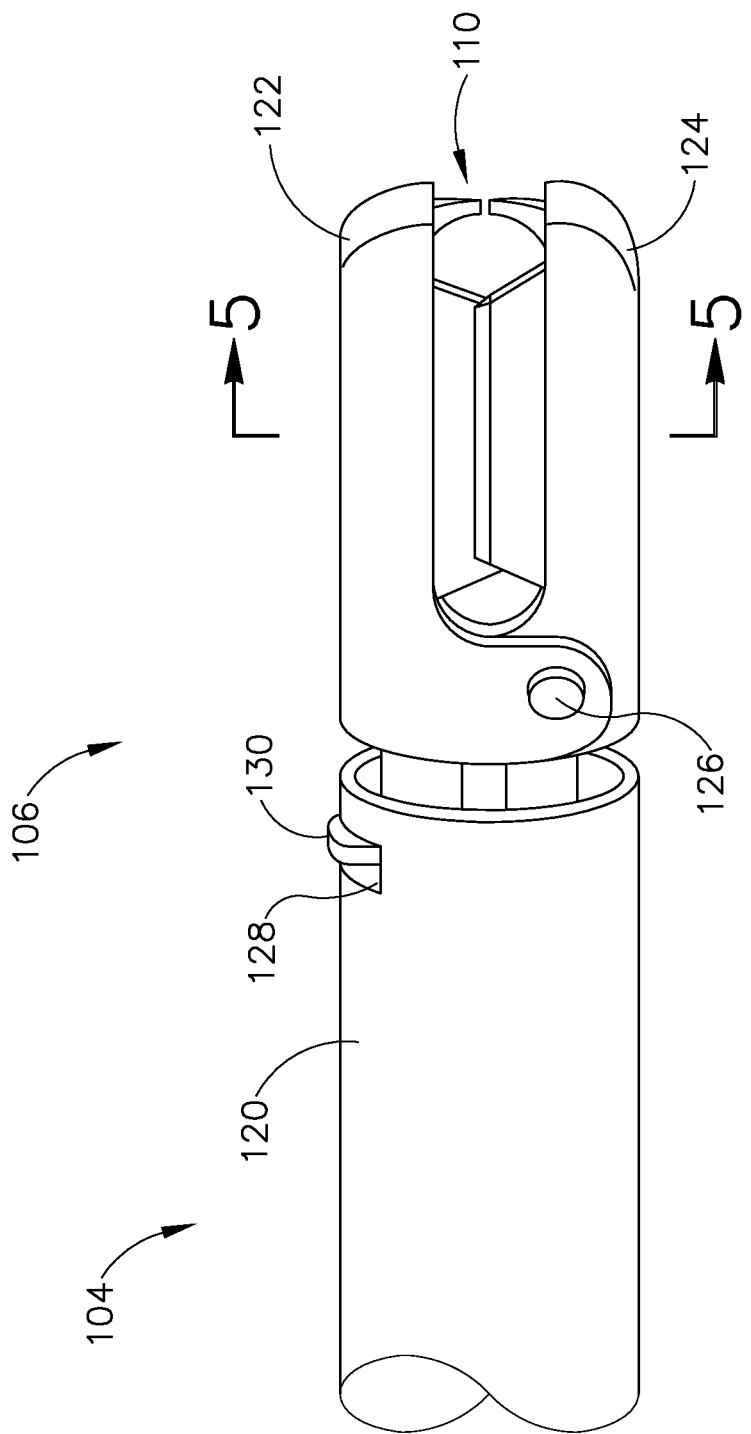
FIG. 3 depicts a side, elevational view of an end effector of the applier of FIG. 1.

End effector (106) comprises an upper jaw (122) and lower jaw (124). FIG. 3 shows an enlarged view of end effector (106), which more clearly shows upper and lower jaws (122, 124). In the exemplary version, lower jaw (124) is pivotally stationary in relation to shaft (104). In some versions, lower jaw (124) may be unitarily constructed with shaft (104) or a portion of shaft (104) to ensure such static positioning. In other versions, lower jaw (124) may be affixed to shaft (104) through bolts, screws, fasteners, etc. such that lower jaw (124) does not pivot in relation to shaft (104). Upper jaw (122) is operable to pivot in relation to lower jaw (124), such that upper jaw (122) is able to move between an open and close position relative to lower jaw (124). In the exemplary version, the pivot (126) between upper and lower jaw (122, 124) is positioned such that pivot (126) is closer to lower jaw (124), but it will be understood that any suitable position for pivot (126) may be used as would be apparent to one of ordinary skill in the art in view of the teachings herein. Furthermore, while upper jaw (122) is movable relative to lower jaw (124), it will be understood that in some versions, lower jaw (124) may be movable relative to upper jaw (122). In yet other versions, both upper jaw (122) and lower jaw (124) may be movable about pivot (126).

Outer tube (120), as mentioned above, is operable to slide along the outside of shaft (104) toward end effector (106). Outer tube (120) is operable to contact upper jaw (122) such that when upper jaw (122) is in an open position, outer tube (120) can be urged against upper jaw (122) to close upper jaw (122) relative to lower jaw (124). Furthermore, outer tube (120) defines a slot (128) operable to couple with a hook (130), which is defined at a proximal end of upper jaw (122). As a result, when outer tube (120) translates proximally, hook (130) catches slot (128) and pulls upper jaw (122) away from lower jaw (124), thereby opening upper jaw (122). Thus, outer tube (120) is operable generally to advance distally in order to close upper jaw (122) against lower jaw (124) and retract proximally to open upper jaw (122) away from lower jaw (124).

III. Exemplary Transecting Fasteners

Figure 2:
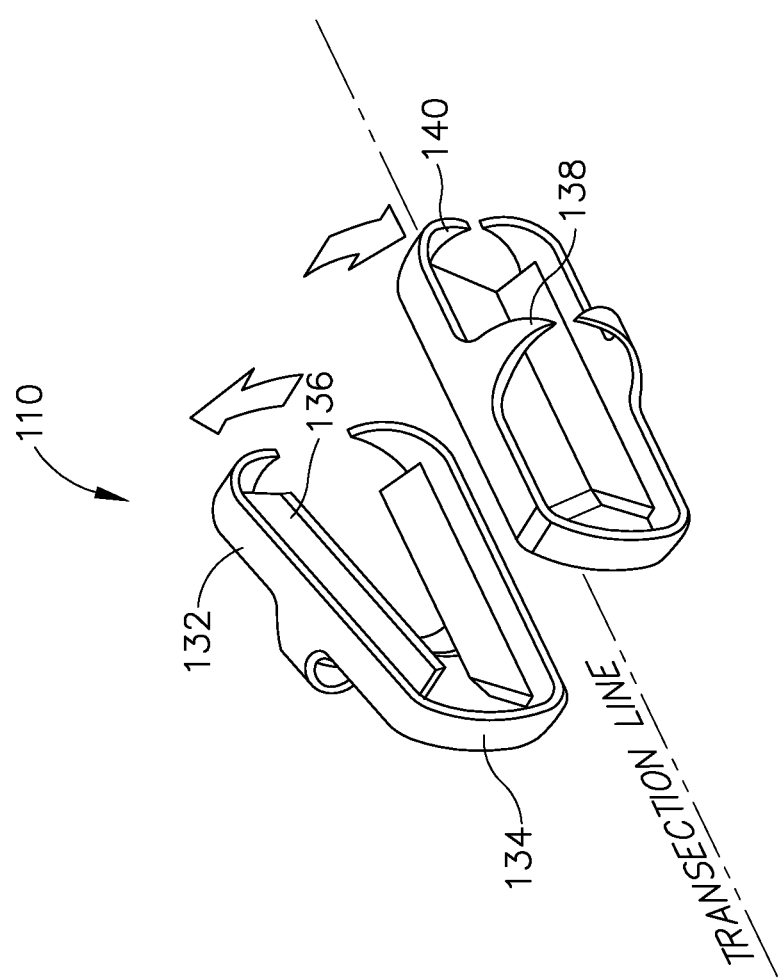
FIG. 2 depicts a top, perspective view of a pair of exemplary transecting fasteners for use with the applier of FIG. 1.

It will be appreciated that the closing motion of upper jaw (124) is operable to close transecting fasteners (110) by deforming fasteners (110) shut. Furthermore, fasteners (110) are malleable such that they maintain a closed configuration when deployed. FIG. 2 shows a pair of transecting fasteners (110). It will be appreciated that transecting fasteners (110) may be used in adjacent pairs as seen in the exemplary version; or may be used one at a time. In yet other versions, more than two transecting fasteners (110) may be used. Indeed, any suitable combination of transecting fasteners (110) may be used as would be apparent to one of ordinary skill in the art in view of the teachings herein.

Fasteners (110) comprise legs (132), a crown (134), blades (136), anchors (138), and front teeth (140). Fasteners (110) are operable generally to cut, compress, and seal tissue in a substantially simultaneous manner. In particular, blades (136) are operable to cut tissue, while anchors (138) and front teeth (140) are operable to seal and grip tissue. Legs (132) are operable to compress tissue therebetween in response to squeezing legs (132) together. Once legs (132) compress tissue, crown (134) is operable to maintain fasteners (110) in a closed and/or clamped configuration around tissue. As mentioned above, it will be appreciated that the stapling and cutting happens in a substantially simultaneous manner. However, it will further be understood that the cutting and stapling may occur at slightly different times based on the relative lengths of blades (136), anchors (138) and front teeth (140). For instance, if blades (136) are much longer relative to anchors (138) and front teeth (140), tissue can be cut and sealed in one motion, but tissue will be cut first immediately followed by being sealed. In the event that anchors (138) and front teeth (140) are much longer relative to blades (136), then it will be appreciated that the stapling action may occur slightly ahead of the cutting action.

Legs (132) and crown (134) form the body of fastener (110). It will be appreciated that crown (134) comprises a malleable material operable to deform to open and close in response to the opening and closing of upper jaw (122) and lower jaw (124). It will be appreciated that crown (134) is sufficiently malleable such that once fastener (110) is bent or otherwise deformed, fastener (110) maintains its bent or deformed shape, sufficient to hold tissue in a clamped configuration. Legs (132) and crown (134) form a generally elongated C-shape profile, but it will be understood that other shapes for fastener (110) may be used as would be apparent to one of ordinary skill in the art in view of the teachings herein.

Anchors (138) have a sharp, hook-like shape. However, it will be understood that any shape operable to anchor into tissue may be used for anchors (138) as would be apparent to one of ordinary skill in the art in view of the teachings herein. Anchors (138) of the exemplary version further extend symmetrically from legs (132) toward each other. While one such positioning of anchors (138) relative to legs (132) is shown in the exemplary version, other suitable positions (e.g., staggered, etc.) may also be used as would be apparent to one of ordinary skill in the art in view of the teachings herein. When inserted into tissue, it will be understood that anchors (138) may grip tissue and may additionally supplement gripping by front teeth (140).

Front teeth (140) have a sharp, hook-like shape. It will be appreciated that any shape suitable for gripping tissue may be used for front teeth (140). As fasteners (110) close from an open position, front teeth (140) pierce tissue and anchor fasteners (110) into the tissue. It will be understood that anchoring in tissue by front teeth (140) may be operable to supplement anchoring by anchors (138). Both front teeth (140) and anchors (138) are constructed such that once anchored into tissue, fasteners (110) are secured into place and maintain their position in the tissue.

Fasteners (110) further comprise blades (136), which are operable to cut tissue as fasteners (110) close against tissue. Blades (136) include an upper blade (142) and a lower blade (144). In particular, blades (136) form a sharp edge operable to slice tissue through shearing. In the exemplary version, blades (136) have a straight cutting edge, but it will be understood that in other versions, any suitable edge or surface may be used to cut tissue as will be apparent to one of ordinary skill in the art in view of the teachings herein. Furthermore, blades (136) of the exemplary version span substantially the length of legs (132). However, in some versions, it will be understood that blades (136) may span only a portion of legs (132). Blades (136) of the exemplary version also have a tapered trapezoid-like shape, but it will be understood that blades (136) may have any suitable shape operable to cut tissue as will be apparent to one of ordinary skill in the art in view of the teachings herein.

Figure 8:
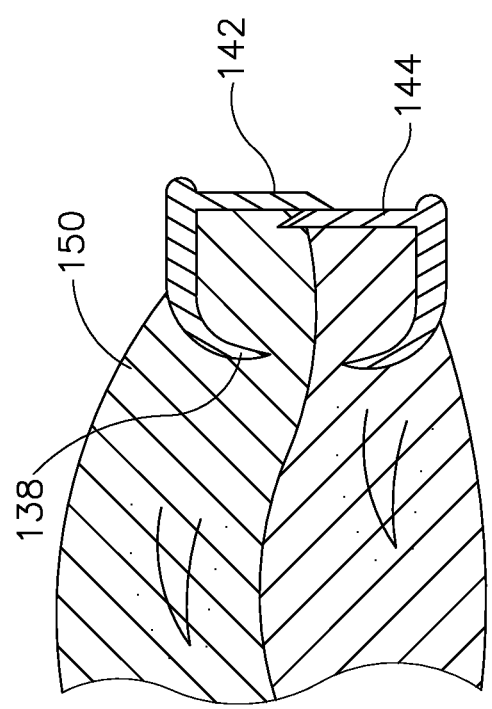
FIG. 8 depicts a front, elevation view of one of the transecting fasteners of FIG. 2, cutting through tissue.

Jumping to FIG. 8, upper blade (142) and lower blade (144) are positioned slightly offset relative to each other such that once upper blade (142) and lower blade (144)

meet, they shear tissue (150), thereby providing the cut. In yet other versions, upper blade (142) and lower blade (144) may be configured in any suitable manner operable to cut tissue as will be apparent to one of ordinary skill in the art in view of the teachings herein. For instance, upper blade (142) and lower blade 9144) may be positioned directly in line with each other along a common plane.

Figure 4:
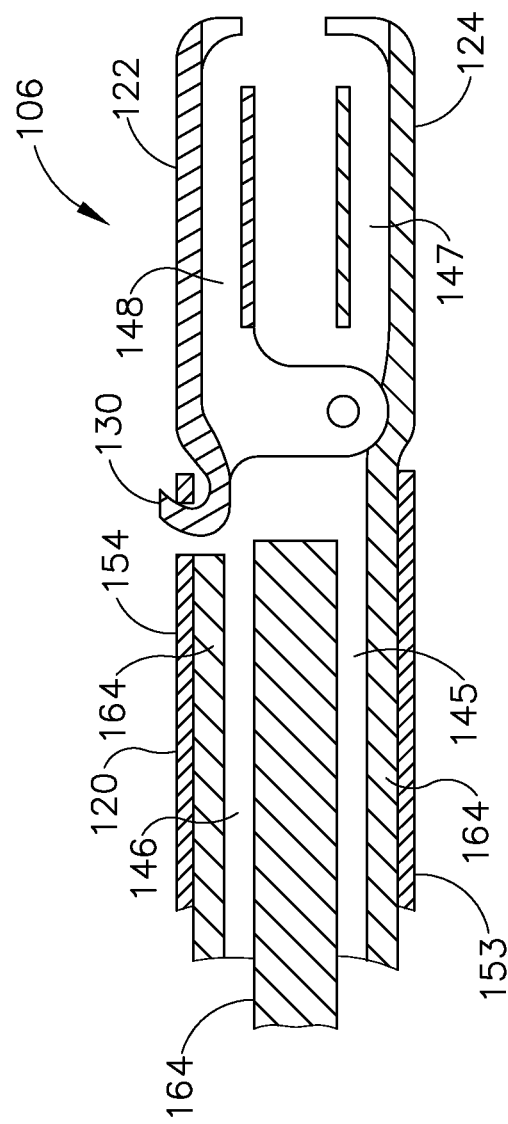
FIG. 4 depicts a side, cross sectional view of the end effector of FIG. 3.

Returning to FIGS. 4-5, end effector (106) is shown in a cross sectional view to show a plurality of fastener channels (147, 148, 151, 152) of end effector (106). Additionally, shaft (104) includes an inner member (164) that defines fastener channels (145, 146, 153, 154). It will be appreciated that inner member (164) is unitarily formed with lower jaw (124). Furthermore, in relation to shaft (104), inner member (164) is operable to rotate with outer tube (120) relative to handpiece (102) as knob (118) is rotated. Thus, inner member (164) is rotationally coupled with outer tube (120). However, inner member (164) and outer tube (120) are not longitudinally coupled, thereby allowing outer tube (120) advance distally and retract proximally in relation to inner member (164) while inner member (164) stays longitudinally stationary. Fastener channels (145, 146, 153, 154) extend longitudinally through shaft (104) and are operable to guide fasteners (110) through inner member (164). Fastener channels (145, 146, 147, 148, 151, 152, 153, 154) are shaped to complement fasteners (110) as seen in the front, cross sectional view shown in FIG. 5. Furthermore, channels (145, 146, 147, 148, 151, 152, 153, 154) are in communication with each other as follows. Fastener channel (145) is in communication with fastener channel (147); fastener channel (146) is in communication with fastener channel (148); fastener channel (154) is in communication with fastener channel (152); and fastener channel (153) is in communication with fastener channel (151).

Figure 5:
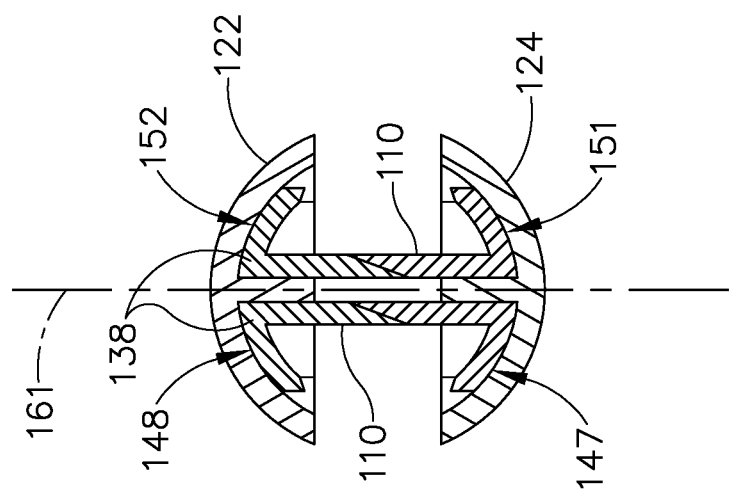
FIG. 5 depicts a front, cross sectional view of the end effector of FIG. 3 taken along the line 5-5 of FIG. 3.

As also seen in FIG. 5, a split axis plane (161) is defined in between channels (145, 146, 147, 148) and channels (151, 152, 153, 154). It will be understood that when fasteners (110) grip and cut tissue, the line of tissue transection lies approximately along split axis plane (161) such that any cuts made by fasteners (110) will be aligned along the longitudinal axis of shaft (104), which overlaps split axis plane (161). Furthermore, fasteners (110) are positioned to exhibit opposing symmetry about axis (161). Fasteners (110) are positioned in a parallel, end to end, arrangement within shaft (104) and end effector (106). More specifically, fasteners (110) are positioned as adjacent pairs with anchors (138) of fasteners (110) oriented outwardly in a manner perpendicular or substantially perpendicular to blades (136). Fasteners (110) are initially positioned in fastener channels (145, 146, 153, 154) of inner member (164) during use of surgical instrument (100), fasteners (110) advance from fastener channels (145, 146, 153, 154) to fastener channels (147, 148, 151, 152) of end effector (106) prior to cutting and sealing tissue. In particular, moving to FIG. 6A, fasteners (110) are shown within fastener channels (145, 146, 153, 154) as well as fastener channels (147, 148, 151, 152). One fastener (110) is shown positioned in end effector (106) whereas another fastener (110) is shown in shaft (104) prior to end effector (106). It will be appreciated that the length of end effector (106) is dimensioned as shown to fit one fastener at a time in end effector (106). It will be understood that in other versions, end effector (106) may be dimensioned to hold more than one fastener (110).

Figure 6A:
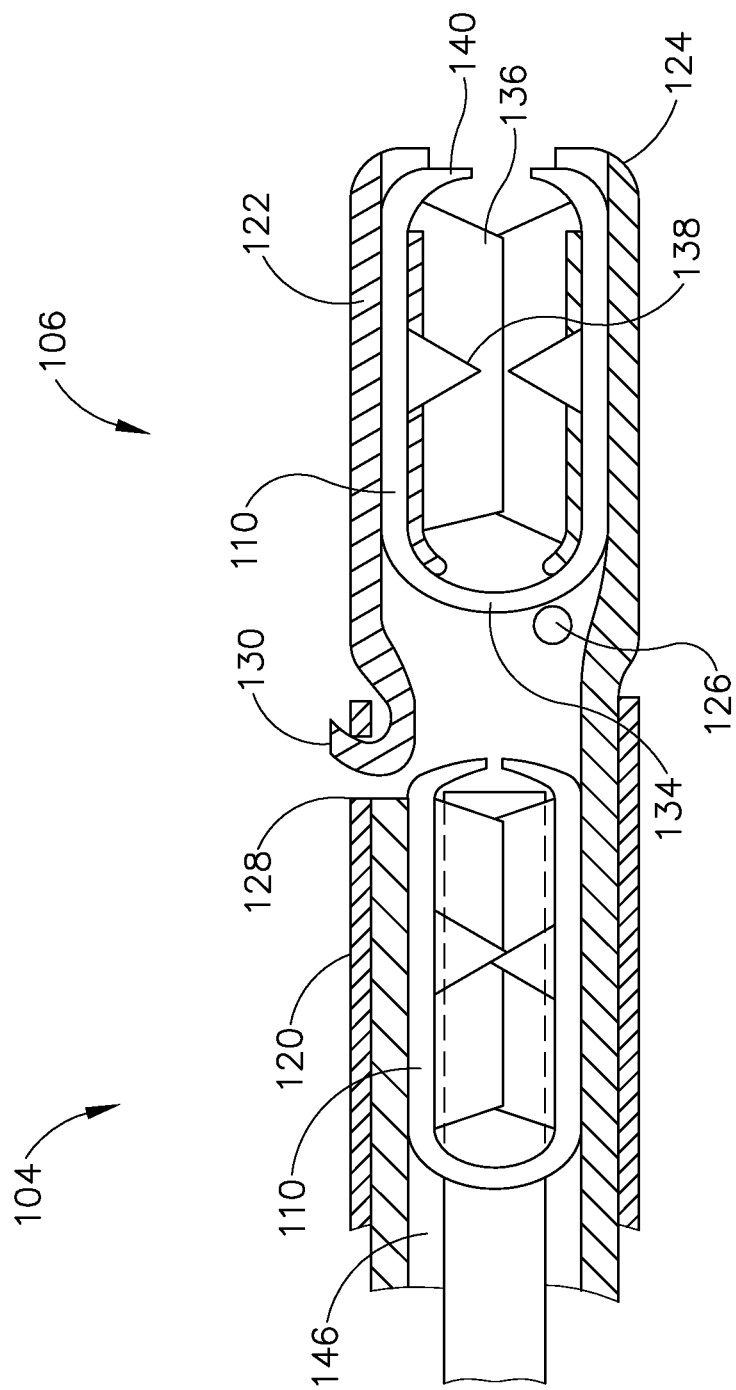
FIG. 6A depicts a side, cross sectional view of the end effector of FIG. 3 in a first position, with transecting fasteners positioned in a guide channel.

As also seen in FIG. 6A, fastener (110) initially starts in a closed position along with end effector (106). Outer tube (120) does not apply sufficient pressure distally or proximally along shaft (104) to cause upper jaw (122) to open relative to lower jaw (124). Once end effector (106) is positioned in an appropriate place in tissue, the user may then actuate closure trigger (116) to open end effector (106). It will be appreciated that closure trigger (116) may be operable to actuate in more than one direction in order to separately open and close upper jaw (122) against lower jaw (124). In the alternative, rather than a single closure trigger (116), more than one closure trigger (116) may be used to separately control the opening and closing of upper jaw (122).

Figure 6B:
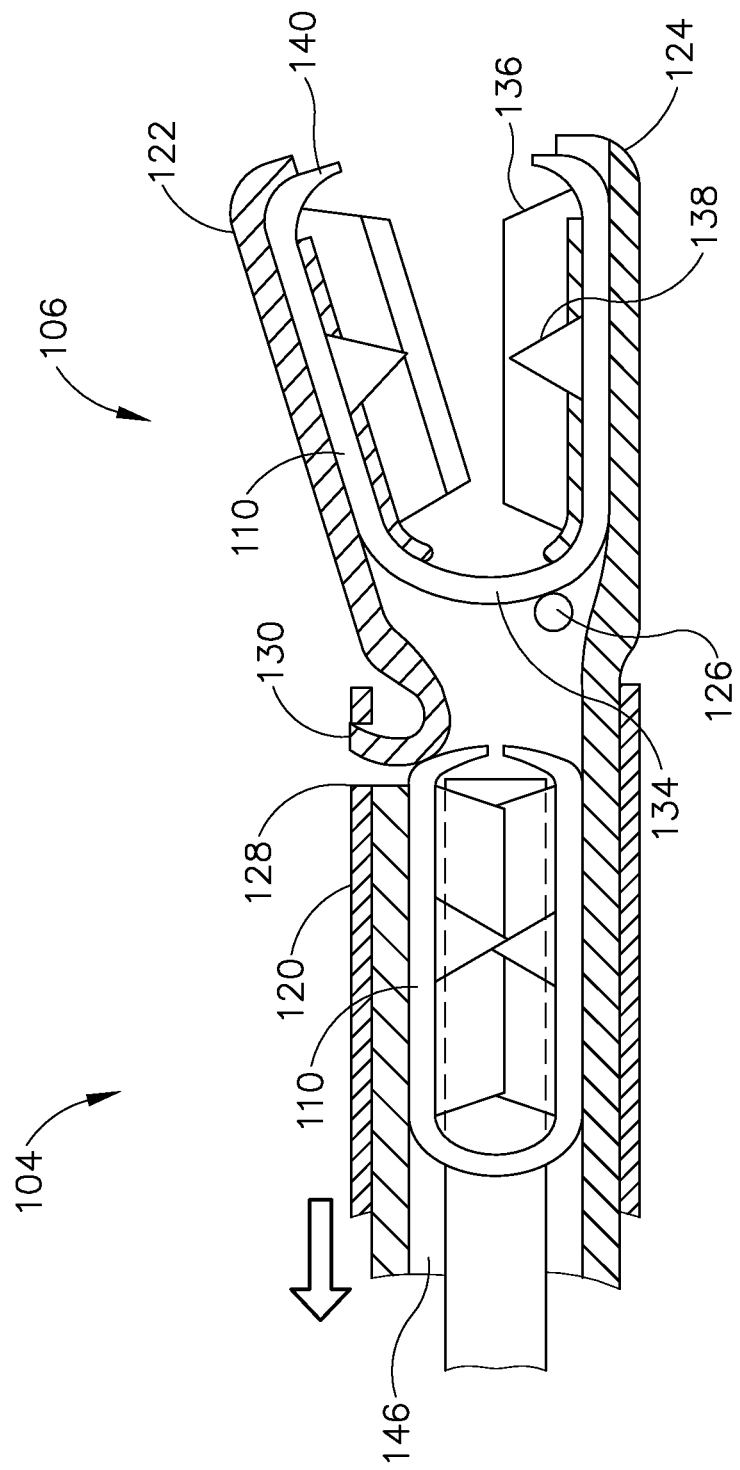
FIG. 6B depicts a side, cross sectional view of the end effector of FIG. 6A in a second position, with the end effector opened.

In the exemplary version, the user actuates closure trigger (116) to cause outer tube (120) to proximally retract. Outer tube (120) catches hook (130) as outer tube (120) retracts and further retracts to pull upper jaw (122) open as seen in FIG. 6B. As upper jaw (122) opens, fasteners (110) positioned in fastener channels (147, 148, 151, 152) of end effector (106) are urged open by upper jaw (122), which separates blades (136) such that fastener (110) is ready for application to tissue.

Figure 6C:
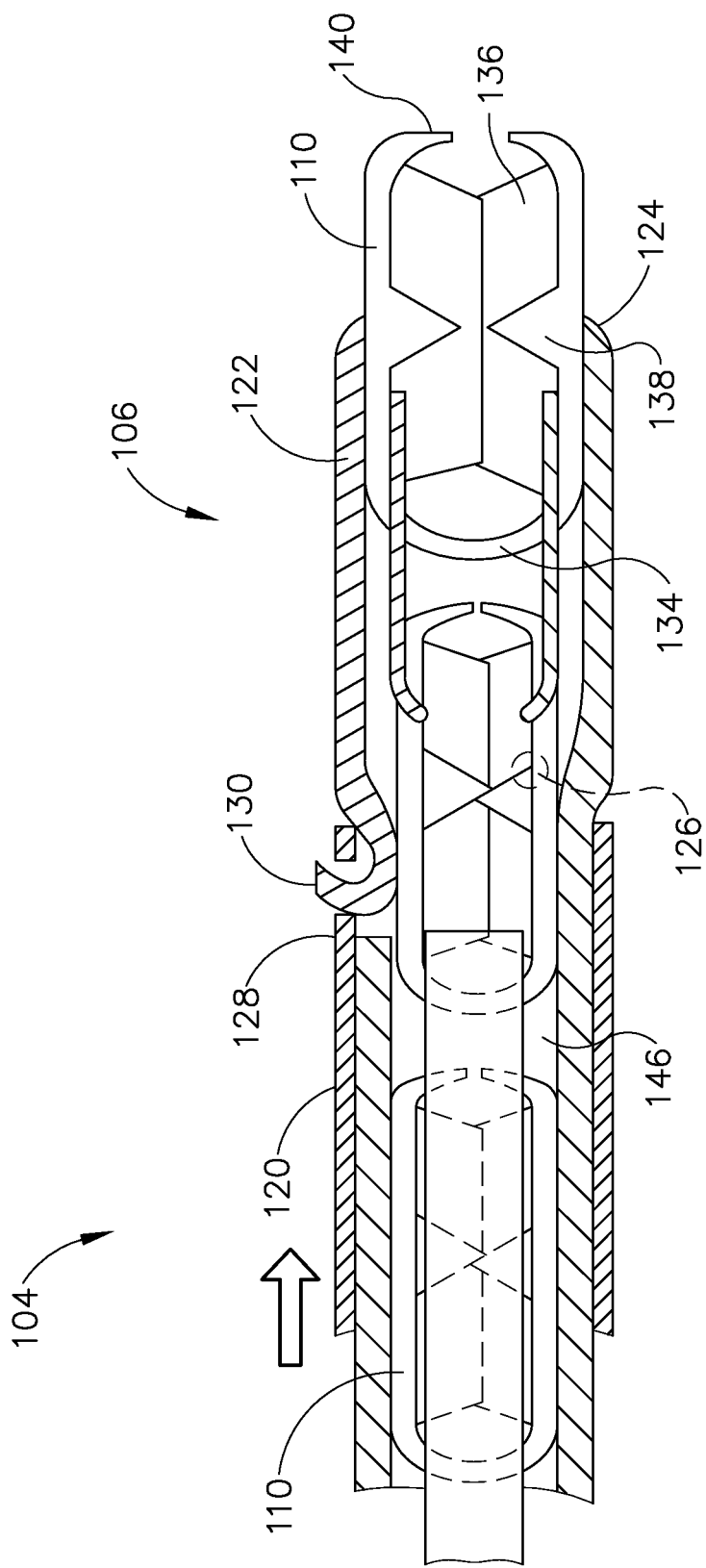
FIG. 6C depicts a side, cross sectional view of the end effector of FIG. 6A in a third position, with the end effector closed and transecting fasteners advanced.

Once end effector (106) is positioned properly around tissue that the user wishes to seal and cut, user may actuate closure trigger (116), which thereby causes outer tube (120) to advance distally as seen in FIG. 6C. The distal edge of outer tube (120) presses against a proximal edge of upper jaw (122), thereby causing upper jaw (122) to pivot toward upper jaw (122) to a closed position. As upper jaw (122) closes, fastener (110) is also urged closed by end effector (106) thereby deforming fastener (110) to a clamped position. As fastener (110) closes, blades (136) cut tissue positioned between upper jaw (122) and lower jaw (124), and furthermore, anchors (138) and front teeth (140) penetrate and anchor themselves into tissue. As outer tube (120) advances to urge upper jaw (122) closed, it will be appreciated that outer tube (120) or some other component of shaft (104) may be coupled with closure trigger (116) to advance a component within shaft (104), such as a rod, etc., which may be used to advance fasteners (110) within shaft (104). For instance, a proximally mounted spring within handpiece (102), a rack and pinion with a ratcheting spring-loaded pawl, or any other suitable means of distally biasing fasteners (110) may be used as would be apparent to one of ordinary skill in the art in view of the teachings herein.

It will be understood that advancement of outer tube (120) is also operable to advance fasteners (110) out of end effector (106) in addition to advancing fasteners (110) within end effector (106). For instance, since fasteners (110) are positioned serially within shaft (104) and end effector (106) in an end-to-end relationship, fasteners (110) may be advanced one pair at a time. Once one pair of fasteners (110) has closed, cut, and anchored into tissue, the next pair of fasteners (110) advances and prepares for opening and closing upon a new portion of tissue. It will be appreciated that the user may repeat the process shown in FIGS. 6A-6C to continue In some instances, a cartridge of staples may be loaded into handpiece (102) to deliver staples. In some instances, the length of shaft (104) and handpiece (102) may be such that the user can cut and seal tissue with fasteners in an effectively indefinitely continuous manner. In some instances, handpiece (102) may be entirely replaceable acting effectively as a reloadable cartridge while shaft (104) and end effector (106) may remain in the surgical site. In yet other instances, handpiece (102) may receive a replaceable cartridge, similar to a handgun ammunition clip, to feed end effector (106) with an effectively indefinite supply of fasteners (110). In addition or in the alternative, a resilient member (e.g., a coil spring, foam, elastomer, etc.) may resiliently bias fasteners (110) distally in shaft (104). As yet another merely illustrative example, one or more features in one or both of jaws (122, 124) may be configured to advance fasteners (110), one pair of fasteners (110) at a time in a side-by-side relationship, each time jaws (122, 124) are pivoted to an open configuration. As yet another merely illustrative example, a twist-pen type of mechanism (e.g., similar to advancement in a ballpoint pen by rotation of concentric tubes, etc.) may be employed to advance fasteners (110) distally. For instance, a rotatable outer tube may be coupled with features on fasteners (110) that convert rotation of the outer tube into distal translation of fasteners (110). Such a rotatable outer tube may be rotated manually or may be automatically rotated each time jaws (122, 124) are pivoted to an open configuration. Other suitable ways in which fasteners (110) may be loaded and/or advanced distally will be apparent to those of ordinary skill in the art in view of the teachings herein. sly cut and seal more portions of tissue.

IV. Transection Fasteners Applied to Tissue

Figure 7A:
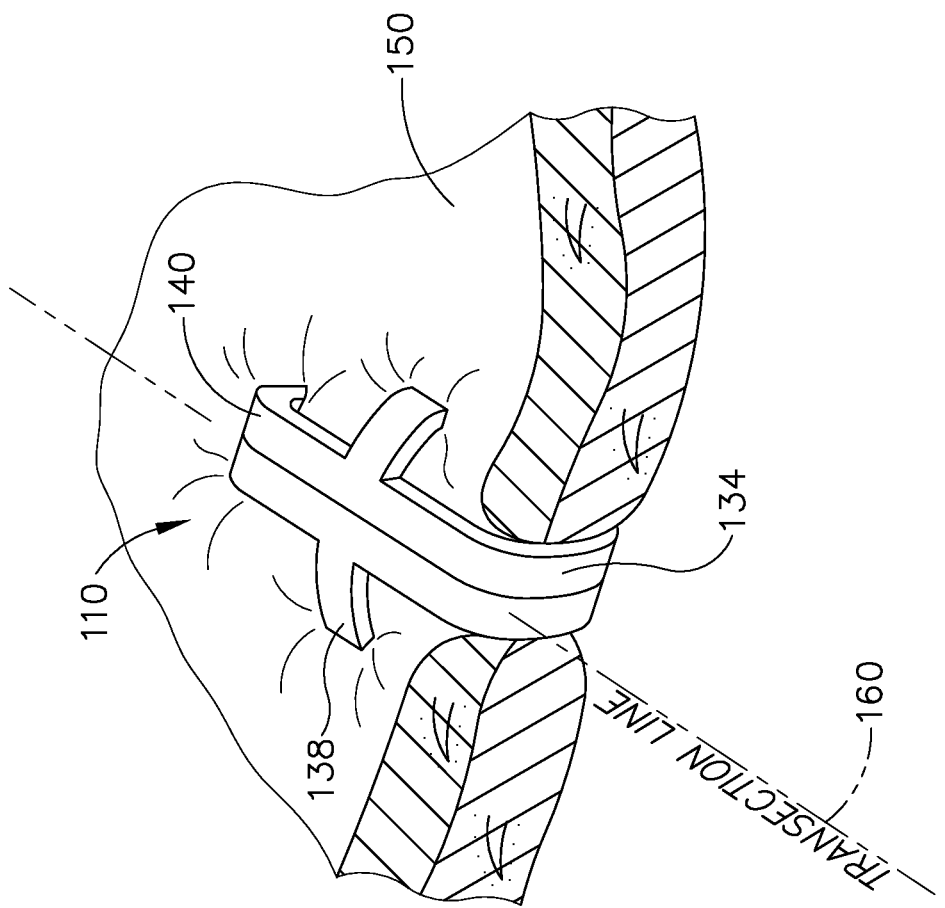
FIG. 7A depicts a top, perspective view of the transecting fasteners of FIG. 2 inserted into tissue.
Figure 7B:
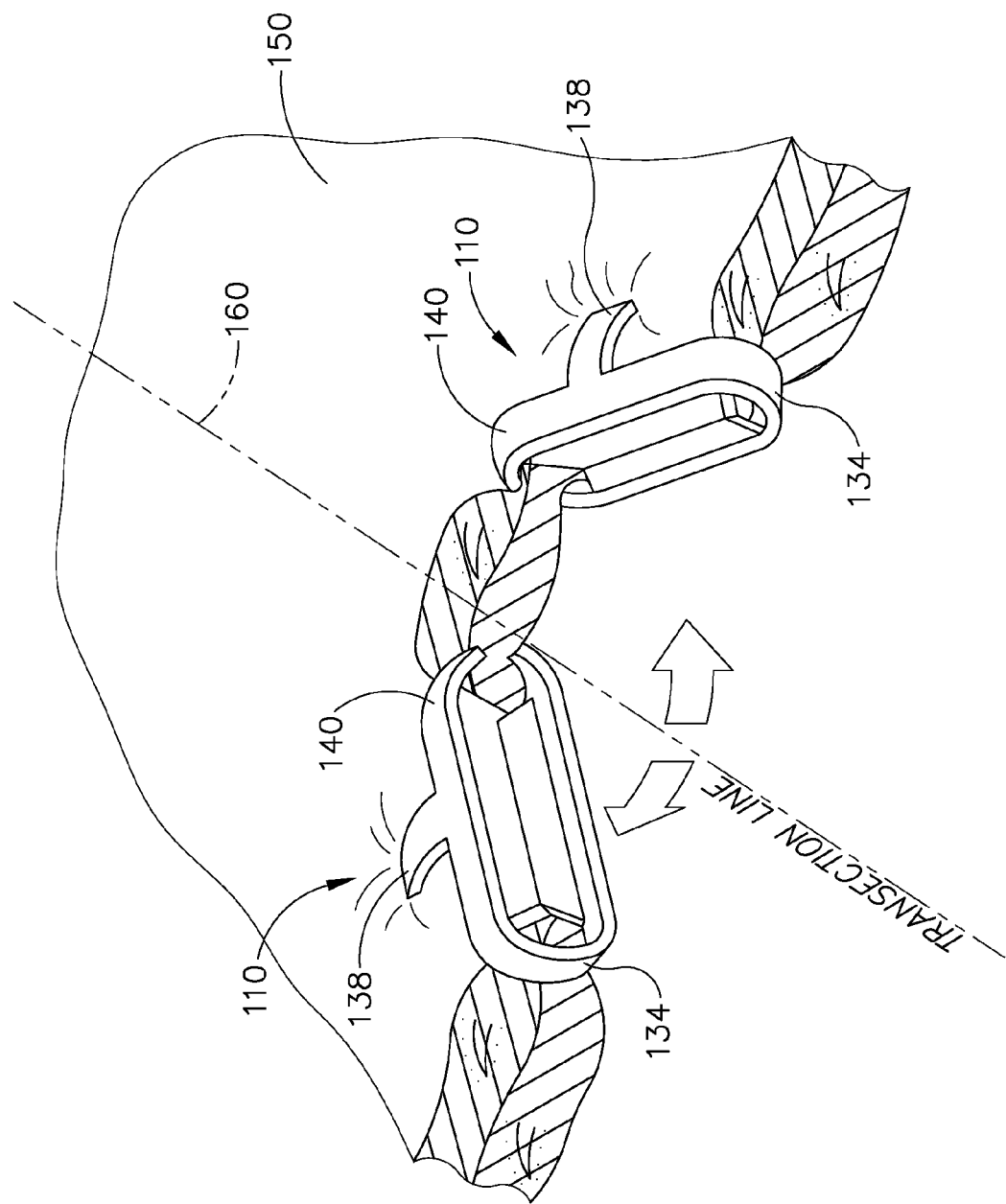
FIG. 7B depicts a top, perspective view of the transecting fasteners of FIG. 7A after cutting tissue and separating the tissue.
Figure 7C:
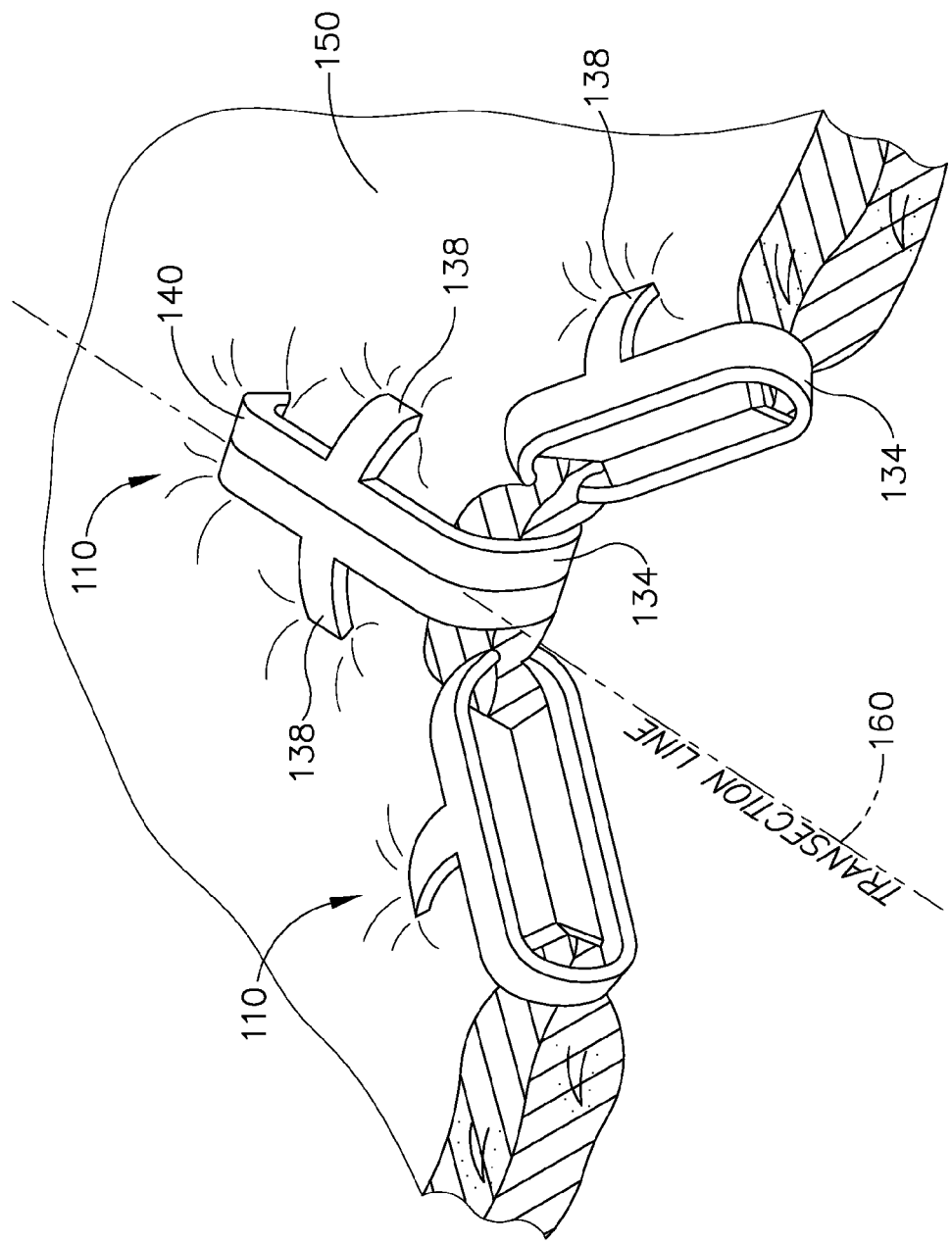
FIG. 7C depicts a top, perspective view of the transecting fasteners of FIG. 7A with the tissue separated and applying a second pair of transecting fasteners.

FIG. 7A shows an exemplary application of fasteners (110) to tissue (150) without showing end effector (106). A transection line (160) is shown merely for demonstrative purposes to show where blade (136) would create a cut within tissue (150). Anchors (138) penetrate tissue (150), thereby securing fasteners (110) in tissue (150). Fasteners (110) are shown cutting and gripping tissue as a matched pair as seen in the illustrative version such that tissue (150) ultimately splits along transection line (160), as shown in FIG. 7B. It will be appreciated that paired fasteners (110) may be split apart as seen in FIG. 7B due to the user forcibly urging apart fasteners (110) after fasteners (110) have cut and anchored tissue (150). In yet other versions, blades (136) of fasteners (110) may cut tissue (150) in a sufficiently clean manner that tissue tension may provide sufficient enough force to pull apart tissue (150) along transection line (160). It will be appreciated that splitting fasteners (110) may be able to provide user visibility of tissue for subsequent stapling. Thereafter, the user may cut and seal another portion of tissue (150), which can be seen in FIG. 7C. While only two pairs of fasteners (110) are shown in the illustrated versions, it will be understood that any suitable number of fasteners (110) may be applied to tissue (150). In fact, fasteners (110) may be continuously added to tissue (150) in order to continue cutting along transection line (160), without having to remove surgical instrument (100) from the patient. It will be understood that to enable continuous application of fasteners (110) to tissue (150), a large number of fasteners may be preloaded such that fasteners (110) can subsequently be delivered along a longer transectional path of any desirable length. For instance, handpiece (102) may be equipped with a continuous feeding mechanism involving a reloadable cartridge, canister, etc. of fasteners (110) that will allow the user to continuously cut and seal tissue with fasteners (110) positioned in an end to end configuration along tissue (150) such that surgical instrument (100) does not need to be removed from the surgical site while completing a substantially long transection (e.g. having a length that would require one or more reloads of a staple cartridge in a conventional endocutter device).

Figure 9:
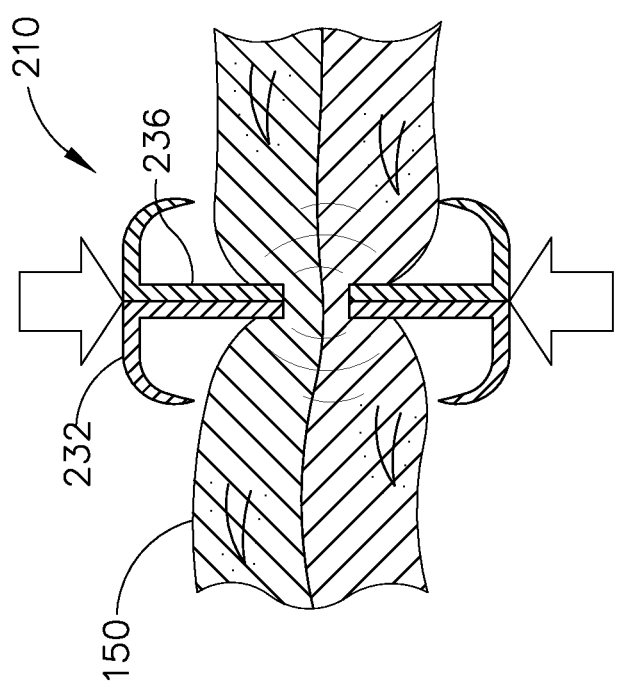
FIG. 9 depicts a front, cross sectional view of an exemplary alternative transecting fastener that is ultrasonically activated, cutting through tissue.

It will be appreciated that in some instances, it may be desirable for fastener (110) to cut tissue (150) through the shearing action of sharp edges of blades (136) of fastener (110). In yet other instances, it may be desirable to cut tissue (150) using electrical assistance. FIG. 9 shows an exemplary alternative fastener (210) having a similar cross section of fastener (110) of FIG. 8. Fastener (210) has legs (232) that are substantially similar to legs (132) of fastener (110). However, fastener (210) comprise a blunt blade (236) operable to cut tissue. In particular, fastener (210) is acoustically coupled with ultrasonic transducer (180) or any other suitable vibrational transducer operable to deliver ultrasonic vibrations to fastener (210). As a result, as blades (236) close upon tissue (150), ultrasonic vibrations of blades (236) facilitate cutting and hemostasis of tissue (150). It will be understood that a particular frequency may be selected for cutting and sealing tissue (150), or a variety of frequencies may be operable to be delivered to tissue (150) for cutting and sealing. It will also be understood that ultrasonic vibrations of blades (236) may include longitudinal vibration, axial or rotational vibration, linear vibration side to side, or any combination thereof as would be apparent to one or ordinary skill in the art in view of the teachings herein.

During an exemplary use, the user could position surgical instrument (100) of FIG. 1 at an appropriate position for cutting tissue (150). Thereafter, energy trigger (114) may be actuated to power ultrasonic transducer (180) within handpiece (102). The transducer could then provide ultrasonic vibrations to end effector (106) and accordingly to fasteners (210) such that closing end effector (106) on tissue (150) is operable to enable the user to cut tissue (150) using ultrasonic vibrations as well as simultaneously anchor fasteners (210) into tissue (150). Furthermore, ultrasonic vibrations could be applied to the surgical site to cause hemostasis of tissue (150), thereby halting tissue bleeding.

Figure 10:
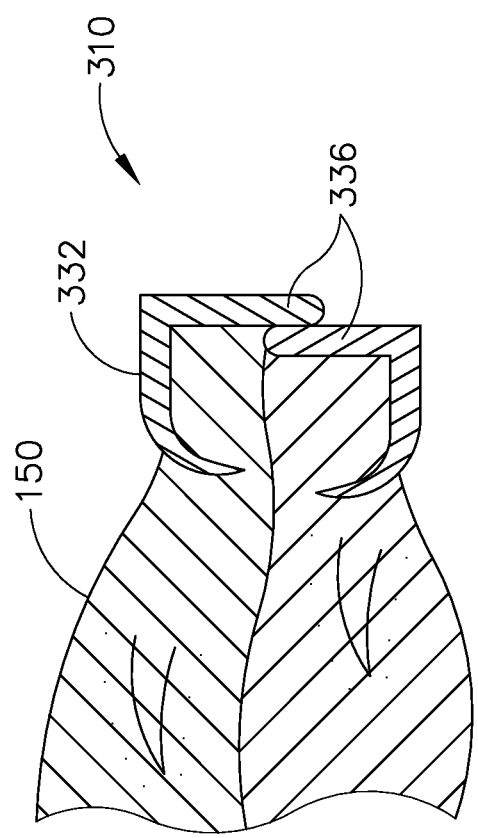
FIG. 10 depicts a front, elevation view of another exemplary alternative transecting fastener that is activated through RF electrical energy, cutting through tissue.

In yet other instances, it will be appreciated that it may be desirable to use RF energy applied to the surgical site to facilitate cutting tissue. FIG. 10 shows an alternative exemplary fastener (310) operable to cut tissue (150) through use of RF energy applied to fastener (310). Fastener (310) comprises legs (332) substantially similar to legs (132) of fastener (110). Fastener (310) comprises a blunt blade (336) operable to cut tissue (150) and deliver RF energy to tissue (150). In the exemplary version, fastener (310) is in communication with RF generator (170) in handpiece (102), which is operable to provide RF energy to fastener (310). As a result, when blades (336) are applied to tissue (150), RF energy is operable to promote cutting and sealing of tissue (150). Furthermore, in some instances, RF energy may also be operable promote coagulation of tissue (150) to prevent or stop bleeding. In some instances, RF energy applied to fastener (310) may include monopolar energy or in other instances bipolar energy. By way of example only, in the case that monopolar energy is applied to the surgical site, a ground pad may be placed on the patient's body or under the patient to provide the electrical ground for delivering monopolar energy. In the case that bipolar energy is applied to the surgical energy, the bipolar energy may be applied directly through fastener (110) where fastener (110) may be constructed such that crown (134) is made of plastic or other suitable insulating material, thereby allowing bipolar RF energy to be applied through legs (132) without shorting at crown (134).

It will be appreciated that RF energy or ultrasonic vibrations as applied to fasteners (210, 310) as described above with respect to FIGS. 9 and 10 may also be applied to end effector (106) or any other suitable portion of surgical instrument (100) as would be apparent to one of ordinary skill in the art in view of the teachings herein.

V. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus operable to cut and secure tissue comprising a transecting fastener wherein the transecting fastener comprises:
    (a) a plurality of legs configured to grip tissue, each of the plurality of legs having an inner longitudinal edge and an outer longitudinal edge;
    (b) a crown portion joining the plurality of legs, wherein the crown portion is deformable; and
    (c) at least one blade positioned on each of the plurality of legs, wherein the at least one blade is spaced in from the inner longitudinal edge and in from the outer longitudinal edge, and wherein the at least one blade is operable to cut tissue.

2. The apparatus of claim 1, wherein each of the plurality of legs comprises a front hook and a side anchor.

3. The apparatus of claim 2, wherein the side anchor is approximately perpendicularly positioned in relation to the front hook.

4. The apparatus of claim 1, wherein the at least one blade is dimensioned to span substantially the entire length of the plurality of legs.

5. The apparatus of claim 1, wherein the plurality of legs are made of a malleable material configured to allow and maintain deformation of the plurality of legs and the crown.

6. The apparatus of claim 1, wherein the plurality of legs and the crown portion form an elongated C shape.

7. The apparatus of claim 1, further comprising a surgical instrument comprising:
    (i) a handpiece,
    (ii) a shaft extending from the handpiece, and
    (iii) an end effector, wherein the end effector is configured to hold at least one of the plurality of legs, wherein the end effector is further configured to drive at least one of the plurality of legs into tissue.

8. The apparatus of claim 7, wherein the shaft comprises an outer tube configured to open and close the end effector.

9. The apparatus of claim 7, wherein the handpiece further comprises an RF generator configured to deliver RF energy to the at least one blade through the shaft.

10. The apparatus of claim 7, wherein the handpiece further comprises an ultrasonic generator configured to deliver ultrasonic vibrations to the at least one blade through the shaft.

11. The apparatus of claim 7, wherein the end effector comprises an upper jaw and lower jaw, wherein the upper jaw is pivotable relative to the lower jaw.

12. The apparatus of claim 7, wherein the handpiece has one or more triggers operable to actuate the end effector using a single-handed operation.

13. The apparatus of claim 7, wherein the shaft defines a split axis plane extending longitudinally through the shaft, wherein the end effector extends distally from the shaft, and wherein the fastener is operable to close along a respective plane that is laterally offset from and parallel to the split axis plane.

14. An apparatus operable to cut and secure tissue comprising a transecting fastener wherein the transecting fastener comprises:
    (a) a plurality of legs configured to grip tissue, each of the plurality of legs having an inner longitudinal edge and an outer longitudinal edge, each of the plurality of legs comprising a front tooth configured to pierce tissue;

(b) a crown portion joining the plurality of legs, wherein the crown portion is deformable; and (c) at least one blade positioned on each of the plurality of legs, wherein the at least one blade is spaced in from the inner longitudinal edge and in from the outer longitudinal edge, and wherein the at least one blade is operable to cut tissue.

15. The apparatus of claim 14, wherein the tooth has a hook shape.

16. The apparatus of claim 14, wherein each of the plurality of legs comprises a side anchor configured to pierce tissue.

* * * * *